United States Patent
Ciurczak et al.

(10) Patent No.: US 8,517,274 B2
(45) Date of Patent: Aug. 27, 2013

(54) DATA WORD ANALYSIS BY SPECTROSCOPY

(75) Inventors: Emil Walter Ciurczak, Golden's Bridge, NY (US); Sharon Flank, Washington, DC (US); William H. Flank, Chappaqua, NY (US); Vojislav Maksimovic, Washington, DC (US); Gary Ritchie, Thurmont, MD (US); Donna Romer, New York, NY (US)

(73) Assignee: Verrana LLC, Silver Spring, MD (US)

( * ) Notice: Subject to any disclaimer, the term of this patent is extended or adjusted under 35 U.S.C. 154(b) by 0 days.

(21) Appl. No.: 13/522,707

(22) PCT Filed: Oct. 15, 2011

(86) PCT No.: PCT/IB2011/054574
§ 371 (c)(1),
(2), (4) Date: Jul. 17, 2012

(87) PCT Pub. No.: WO2012/049666
PCT Pub. Date: Apr. 19, 2012

(65) Prior Publication Data
US 2012/0286046 A1    Nov. 15, 2012

Related U.S. Application Data

(60) Provisional application No. 61/455,095, filed on Oct. 15, 2010, provisional application No. 61/454,854, filed on Mar. 21, 2011.

(51) Int. Cl.
*G06K 19/06*    (2006.01)
*G01T 1/161*    (2006.01)

(52) U.S. Cl.
USPC ............................................ 235/491; 250/302

(58) Field of Classification Search
USPC ........................... 235/454, 491; 250/302
See application file for complete search history.

(56) References Cited

U.S. PATENT DOCUMENTS

| | | | |
|---|---|---|---|
| 7,420,663 B2 | 9/2008 | Wang et al. | |
| 7,985,590 B2 * | 7/2011 | McNeil | 436/58 |
| 2005/0143249 A1 | 6/2005 | Ross et al. | |
| 2006/0196936 A1 | 9/2006 | Christofferson et al. | |
| 2009/0218391 A1 | 9/2009 | He | |
| 2010/0258718 A1 * | 10/2010 | Welle | 250/302 |

FOREIGN PATENT DOCUMENTS

| | | |
|---|---|---|
| WO | 9526018 A1 | 9/1995 |
| WO | 0214812 A1 | 2/2002 |
| WO | 0216905 A2 | 2/2002 |
| WO | 03087740 A1 | 10/2003 |

(Continued)

OTHER PUBLICATIONS

International Search Report in international application No. PCT/IB2011/054574, mailed Apr. 25, 2012.

(Continued)

*Primary Examiner* — Daniel Hess
(74) *Attorney, Agent, or Firm* — Oppendahl Patent Law Firm LLC

(57) ABSTRACT

Multisource fusion of data is used on a handheld device to create a portable analytical verifier, including the ability to verify based on product wrapping or using a re-turned code to check the product or wrapping. Data words are extracted from authentication media by testing to see whether particular taggants are present, using spectroscopic analysis.

16 Claims, 9 Drawing Sheets

(56) References Cited

FOREIGN PATENT DOCUMENTS

| WO | 03094679 | A2 | 11/2003 |
| WO | 2004023974 | A2 | 3/2004 |
| WO | 2004069164 | A2 | 8/2004 |
| WO | 2008113962 | A1 | 9/2008 |
| WO | 2009111579 | A2 | 9/2009 |

OTHER PUBLICATIONS

Written Opinion of the International Searching Authority in international application No. PCT/IB2011/054574, mailed Apr. 25, 2012.

* cited by examiner

DATA WORD ANALYSIS BY SPECTROSCOPY

CROSS-REFERENCE TO RELATED APPLICATIONS

This application is a non-provisional application claiming the benefit of U.S. application No. 61/454,854 filed Mar. 21, 2011 and U.S. application No. 61/455,095 filed Oct. 15, 2010, each of which is incorporated herein by reference for all purposes.

BACKGROUND

The present invention relates generally to the field of spectroscopy. It is known that a spectrometer may be used to identify one or more compounds based on the spectral profile of absorption or emission. It is also known that spectrometers may be hand-held devices and may be communicatively linked with a computer or telephone via wireless networking. One patent of interest might include U.S. Pat. No. 7,420,663. However, it has not been possible, heretofore, to spectroscopically encode or decode a message or to provide efficient product authentication using spectroscopy, and further to integrate portable spectroscopy with many sources of data to enhance verification and tracking.

In a world in which products may be contaminated, adulterated, counterfeited, or mislabeled, consumers are increasingly searching for reassurance about what they buy and what they eat. It is desirable to provide fast, in situ verification.

Methods such as RFID (radio frequency ID) only apply to the containers, not the contents. If the drug materials are removed and replaced, container security is useless. However, if the shrink-wrapped "tamper-resistant" seal is tagged in a proprietary manner, the materials within can be assumed "unadulterated."

One established form of authentication is tamper-resistant packaging. A common solution is through film wrappers, a transparent film is wrapped securely around the entire product container. The film must be cut or torn to open the container and remove the product. A tight "fit" of the film around the container must be achieved, e.g., by a shrink-type process. In selecting methods of packaging authentication it is important to minimize the possibility that the material or a facsimile may be broadly available or susceptible to imperceptible removal and reapplication. For example, a film wrapper sealed with overlapping end flaps must not be capable of being opened and resealed without leaving visible evidence of entry. Heat-shrink bands or wrappers may be employed for authentication. A band or wrapper is securely applied to a portion of the container, usually at the juncture of the cap and container. The band or wrapper is heat shrunk to provide a tight fit. It must be cut or torn to open the container and remove the product and the wrapper cannot be worked off and reapplied without visible damage. The use of a perforated tear strip can enhance tamper-resistance.

Whole boxes or even pallets may be shrink-wrapped. Wrap types include, but are not limited to, shrink bands, shrink sleeves, tapes, and security seals. Typically these wraps, once broken, cannot be replaced.

To further prevent tampering the film wrapper may employ an identifying characteristic that cannot be readily duplicated. This may include imbuing the film with an identifying characteristic that is proprietary and different for various products. Current identifying characteristics include color or imprinted characters on the wrapping material.

Counterfeiting is a large and growing problem. Current solutions have focused on the cardboard packaging or special stickers, but not on the outer wrap, and, so far as the applicants are aware, no anti-counterfeiting approach to date has used covert spectroscopic tagging of the wrap layer. There are several reasons for this: large lab spectrometers have been useful for forensic testing, but not for field testing. The test personnel have been "mystery shoppers," either security staff or field sales personnel, who select suspect containers, purchase them, and send them back to a lab for forensic analysis, which often includes spectroscopy.

The existing state of the art in spectroscopy, whether desktop, in-process, portable, handheld, or cell phone, acquires spectral information and then processes it either locally or, if remotely, with respect to a single reference source. Spectroscopy has only recently become usable outside the laboratory. Newer portable and handheld spectrometers have focused on ease of use, to enable inspectors and lab assistants to collect spectroscopic data on material composition.

Some background regarding spectroscopy may be found in previous patent filings of one or another of the present inventors, for example WO 2009111579 entitled "Spectrometric methods and apparatus", WO 2004069164 entitled "Wireless blood glucose monitoring system", WO 2004023974 entitled "Apparatus and method for non-invasive measurement of blood constituents", WO 2003094679 entitled "Spectroscopic analyzer for blender", WO 2003087740 entitled "Method and apparatus for determining the homogeneity of a granulation during tableting", WO 2002016905 entitled "Near infrared blood glucose monitoring system", WO 2002014812 entitled "Automated system and method for spectroscopic analysis", and WO 1995026018 entitled "Fluid, gas or vapor diagnostic device.

In the current state of the art, spectra are collected with a spectrometer. Chemometric processing is then performed in one of two ways: either it is managed on a computer directly embedded in the spectrometer, or file(s) are downloaded and made available for chemometric processing. In contrast, many of the embodiments described herein employ wireless communications integrated with the hand-held spectrometer to enable sending the data to a remote chemometrics processor, where the chemometrics processor accesses a model and sends the analyzed data back to the cell phone spectrometer in real time.

Real-time chemometrics makes it possible to update the model, and enables results from miniature and portable spectrometers. Building upon the emerging portability and simplicity makes it possible for consumers to use spectroscopy for new and unforeseen applications.

SUMMARY

In contrast to older approaches, many of the embodiments described herein employ wireless communications integrated with the hand-held spectrometer to enable sending the data to a remote chemometrics processor, where the chemometrics processor creates a model and sends the analyzed data back to the cellphone spectrometer in real time. Real-time chemometrics makes it possible to adjust the model, and enables a new level of quality results from small, portable, and not necessarily highly accurate spectrometers. Building upon the emerging portability and simplicity makes it possible for consumers to use spectroscopy for new and unforeseen applications.

The following embodiments and aspects thereof are described and illustrated in conjunction with systems, tool and methods which are meant to be exemplary and illustrative, not limiting in scope. In various embodiments, one or more of the above described problems have been reduced or eliminated, while other embodiments are directed to other improvements.

Spectroscopy technology is desirable as an approach for anti-counterfeiting and verification measures. Ideally, the basic device is a portable, preferably handheld, self-powered device that could be configured to work with, or integrated into, a cell phone. The components for the device may comprise the following:

- Optical bench (baseplate or stage),
- Power source (battery),
- Light source (light emitting diode (LED that is commonly referred to as a blue LED pumped fluorescent light source, dubbed a white LED),
- Converter,
- Diffraction Grating or Filter (Linear Variable Filter (LVF)),
- Processor coupled to a Detector (Charged Couple Device (CCD) or complementary Metal Oxide Semiconductor (CMOS), and
- Software.

Several issues associated with the device that must be considered and assessed for optimal performance include: If using infrared, Autofocus IR is based on Broadband IR, so one would need a mechanism to change broadband to discrete wavelengths such as linear variable filters (LVFs), stray light, noise, resolution, dynamic range, linearity and saturation. Many standards are available for such assessment by national bodies such as the National Institute of Standards and Technology (NIST) and private non-governmental organizations for assessing instrument performance for commercial use.

The device should be able to illuminate the sample, and convert the reflected, emitted, or absorbed energy (infrared, fluorescence, or UV/visible) to a digital signal that can be processed and analyzed. The analysis may be based on chemometric approaches that process linear or non-linear algorithms, used to deconvolute the univariate or multivariate raw data.

The addition of multisource fusion of spectral data with secondary data is a valuable feature, incorporating different kinds of information from sensors, databases, other users, and the internet to assist in verification and tracking. Additional, non-spectroscopic information is fused with the spectral data to yield actionable results. In the past, the only kind of data used with spectroscopy has been spectral: is this result comparable to a previous result? Is this specimen spectrally the same as the gold-standard specimen? Previously, association of spectral data with secondary data was not automated.

Embodiments of the current disclosure perform data fusion by bringing in non-spectral information to add data about other properties.

The multisource fusion may include data processing with a software system, and libraries for vertical applications. It also may incorporate imaging tools with a network connection to a database; field data, plus public source data, plus aggregate consumer data, all then added to knowledge that the other multisource fusion data adds, plus crowd-sourcing, possibly including a smart-crowd, i.e., a knowledgeable group, for example pharmacists.

The hardware can comprise an integrated infrared camera and light source, already available in some digital cameras and even some smart phone cameras, collimator, lens, sensor, display, etc. Alternatively, a spectrometer attachment may be communicatively coupled with a cellular telephone, for example by Bluetooth or by tethered cable connections.

Some embodiments of the present disclosure provide novel identifying characteristics using the wrap layer of packaging around items of interest, whether on the individual unit or on larger groups of units, as an information-containing security device. Some embodiments employ multisource fusion, incorporating spectral information with additional kinds of information from sensors, databases, other users, and the internet to assist in verification and tracking.

Incorporation of specific, chosen additives into the polymeric material comprising a wrapping material makes it possible to create a code. The polymer's ingredients may be intentionally varied to create the code, or additives themselves may also be included as part of the coding. These ingredients, such as antioxidants or chemicals which give structural strength, are easily varied in concentration when the particular lot of shrink wrap is formulated. Since the molten polymer is truly a solution, the ratios of the chemicals can be controlled to very fine levels. The additives and/or other ingredients are chosen such that they have distinctive chemical attributes, including, but not limited to, spectral features in, for instance, the UV, near-infrared, Raman, or infrared regions of the electromagnetic spectrum; fluorescing materials can also be used. The use of ion mobility spectrometry is an additional option. Using a non-destructive analytical method including, but not limited to, near-infrared spectroscopy, Raman spectroscopy, UV-Vis spectroscopy, and x-ray or classic fluorescence, a tester or inspector could determine instantly whether the correct wrap was on the product, preferably using a handheld instrument, including a smartphone. The wrap itself may be plastic (polymer), petroleum-derived or biologically-derived.

Many of the disclosed embodiments make use of portable spectrometers, enabling field testing. The wrap layer is altered to include non-essential additives, which serve as a covert authenticity tag. Unlike the vast majority of anti-counterfeiting measures, these additives are not rendered ineffectual if a counterfeiter should discover them, because they form a coding language, rather than a single special-ingredient tag. If a covert spectroscopic wrap tag is somehow discovered by a counterfeiter (this is difficult and expensive, but not impossible), the manufacturer can simply switch to another of millions of possible codes. Periodic code changes may be applied.

Some wrap options include printing the label itself as shrink-wrap. In this case the color components of the label would simply serve as additional data points in the visible spectrum, able to convey additional information as needed. Different tints might indicate different doses or package sizes, for example, offering an additional layer of error-protection as well as the coding. Aftermarket wrapping by others would not have the right chemical signature, so anyone breaking the seal would not be able to replace the correct mixture, even if they had access to a shrink-wrap machine.

Since the original wrapping material cannot be re-used, a quick scan, or missing wrapping, would show if a bottle had been tampered with. The wrap could be used, for example, on the nipple of an IV bag. The FDA's definition of "adulteration" includes package flaws, so smartwrap scanning would indicate an adulterated package, without any need to open the package unless additional testing of the contents is desired.

The present disclosure also describes methods for direct analysis of products utilizing integrated data sources.

In addition to the exemplary aspects and embodiments described above, further aspects and embodiments will become apparent by reference to the accompanying drawings forming a part of this specification wherein like reference characters designate corresponding parts in the several views.

BRIEF DESCRIPTION OF THE DRAWING

The invention is described with respect to a drawing in several figures. Where possible, like elements among the figures are denoted with like reference numerals.

DETAILED DESCRIPTION

Figure 1:
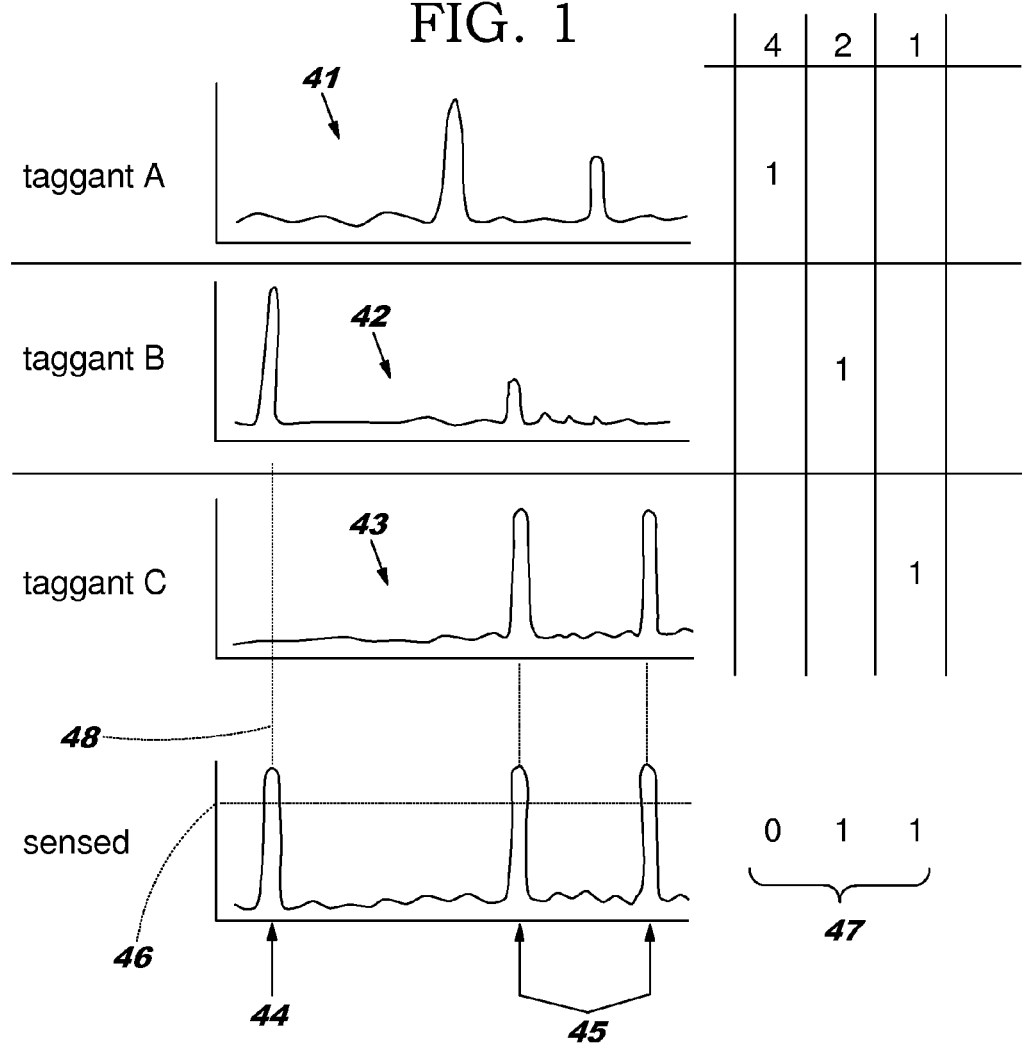
FIG. 1 portrays the "data word" aspect of a method according to the invention.

Turning to FIG. 1, we see the "data word" aspect of a method according to the invention. This presentation is oversimplified for clarity of presentation, assuming a universe of but three taggants A, B, and C. (In real implementations the universe of possible taggants might be ten or twenty in number.) Given some standard excitation (illumination) the spectroscopic activity of taggant A is shown in spectrograph 41. The spectroscopic activity of taggant B is shown in spectrograph 42. The spectroscopic activity of taggant C is shown in spectrograph 43.

Assume for sake of discussion that taggants B and C are present in the authentication medium of interest, and that taggant A is absent. The resulting spectrograph 48 will be, to a first approximation, a linear combination of spectrographs 42 and 43 together with other data values which, it is hoped, do not make it impossible to pick out taggants A, B, and C if any of them is present. In this particular case a peak at 44 indicates the presence of taggant B and peaks at 45 indicate the presence of taggant C.

Predetermined power-of-two binary values are assigned to the taggants. Taggant A in this example is a binary "one" associated with two to the second power, Taggant B in this example is a binary "one" associated with two to the first power, and Taggant C in this example is a binary "one" associated with two to the zeroeth power. Thus with detection of taggants B and C the resulting binary number is "011" or decimal 3.

In this embodiment the spectroscopic analysis is carried out with respect to a threshold 46, selected with the hope that the threshold will permit a simple "present" or "not present" conclusion as to particular peaks. The threshold may need to be scaled in real time to accommodate such things as variations in the quality of the optical coupling of the spectroscope with the authentication medium of interest, or variations in the intensity of the stimulation light source. But as will be discussed at some length below, for many embodiments the design goal is for the spectroscope to be simple in physical design, modest in cost, and limited in the required level of accuracy. As such the threshold may be a fixed threshold predetermined at the time of design or at the time of manufacture.

If ten taggants make up the universe of possible taggants, then as many as 1024 (two to the tenth power) distinct binary numbers could be developed. The alert reader will appreciate, however, that some of the 1024 values would likely not be put into actual use in the labeling of an authentic product. For example the value composed of all zeroes would likely not be put into actual use since it would be indistinguishable from a result where (for example) some physical barrier happens to have blocked the light path of the system, unbeknownst to the user. Similarly the values composed of a single taggant (and the absence of the other taggants in the universe of taggants) might not be put into actual use on the theory that accidental materials combinations might satisfy the threshold for a single taggant, or for other reasons.

Figure 2:
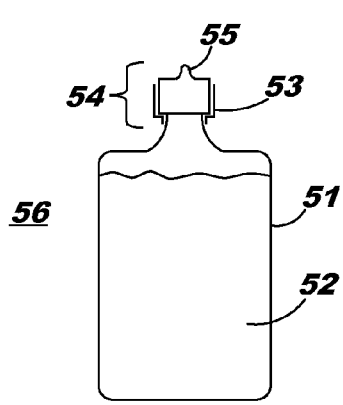
FIG. 2 shows in cross section a bottled consumer product with a neck band.
Figure 3:
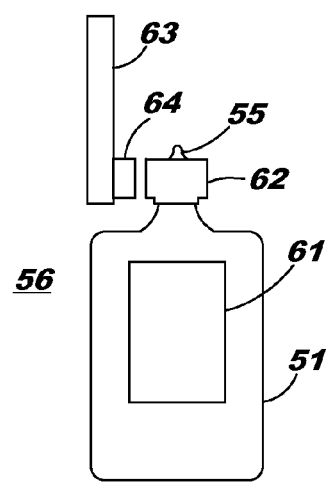
FIG. 3 shows a smart phone according to the invention applied toward the product of FIG. 2.

FIG. 2 shows in cross section a bottled consumer packaged good 56 with a bottle 51 with a neck band 53. The content 52 of the bottle might be contact lens solution. The neck area 54 has a screw-top cap 55. A shrink-wrap band 53 has been shrunk onto the neck area 54. FIG. 3 shows a smart phone 63 according to the invention applied toward the product 56 of FIG. 2. A label 61 might be genuine or might be a counterfeit label, in the latter case because the content 52 is counterfeit. Alternatively the content 52 might originally have been authentic but might have been tampered with.

In the event of a genuine (authentic) product the neck band 62 will have taggants (omitted for clarity in FIG. 3) selected by the manufacturer from among some universe of taggants. When the smart phone 63 (which has a spectroscope 64) is applied to the neck band, the spectroscope carries out an analysis and develops a binary number as a result of the analysis. The binary number will, it is hoped, permit the user to know that the product is genuine.

In the event of a counterfeit product the neck band 62 will likely not contain any of the taggants. The smart phone develops the binary number zero and this permits the user to know that the product should not be used.

In the event of a tampered-with product the neck band 62 once again will likely not contain any of the taggants, because the tamperer will have had to remove the genuine neck band and will have had to apply a new (non-tagged) neck band in its place. The smart phone again develops the binary number zero and this permits the user to know that the product should not be used.

Speaking in general terms, we see a package having a sealing location, and the authentication material is a shrink-wrap band, the shrink-wrap band shrunk upon the sealing location. In this specific case the package is a bottle with a screw-top cap at a neck thereof, and the sealing location is the neck of the bottle.

Figure 4:
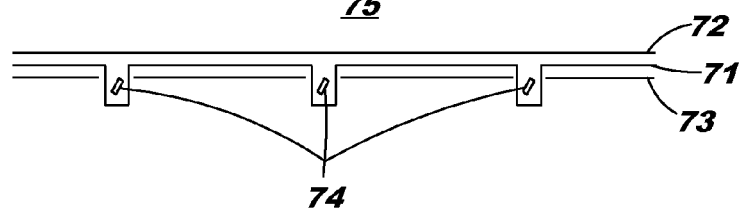
FIG. 4 shows in cross section a blister pack according to the invention.

FIG. 4 shows in cross section a blister pack 75 according to the invention. A (typically) clear plastic tray 71 is stamped from sheet stock, providing wells in which pills 74 may be placed. Cardboard layers 72, 73 are glued or laminated to the tray. The cardboard layers permit human-visible labeling, marking of particular wells with days of the week, and so on. As in the previous example, taggants are selected by the manufacturer of the pills or, in this case, by the maker of the blister pack (which might or might not be the manufacturer of the pills). The taggants are joined to an authentication medium, and the authentication medium is made part of the blister pack. One approach to this end is to apply the selected taggants to the inside surface of the tray 71, or within the material of the tray 71, or upon the outside surface of the tray 71. Another approach is to join the taggants to the layer 72 which might be clear plastic instead of cardboard, again on an inner surface, or within the material, or on an outer surface. Still another approach is that the taggants are joined to a clear layer (omitted for clarity in FIG. 4) that is laminated (by heat and pressure) or glued (or both) to the cardboard layer 72.

The alert reader will appreciate that many of the materials choices may be varied. In this example the layers 72 and 73 are described as cardboard but of course other materials such as plastic or paper may serve. Likewise there may be more layers (for example foil layers) above or below the tray layer. Most of these and other variations will not depart from the invention as described.

Figure 5:
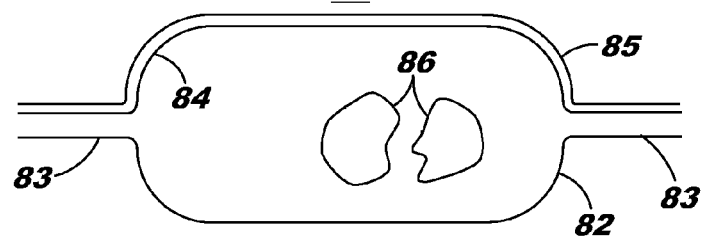
FIG. 5 shows a bagged product according to the invention.

FIG. 5 shows a bagged product according to the invention. We see a bag 81 made of front layer 84 and rear layer 82, sealed at sealing locations 83, typically by heat sealing. The bag has contents which may be edible items 86 such as chips, or may be drinkable or otherwise consumable. In accordance with the invention, one of the layers such as top layer 84 may be joined with taggants for use in authentication. In another approach, an authentication medium 85 may be laminated onto top layer 84, itself joined with taggants for such use. As for the layer with which the taggants are joined, the taggants may be on an inside face thereof, or may be on an outside face thereof, or may be disposed within the material thereof.

Saying this in different words, the first authentication material may be a sheet, and the package may contain a consumer product, and the sheet may be laminated to a face of the package. The package may be a flexible heat-sealed bag and the consumer product may be an edible or drinkable or consumable product within the bag.

Figure 13:
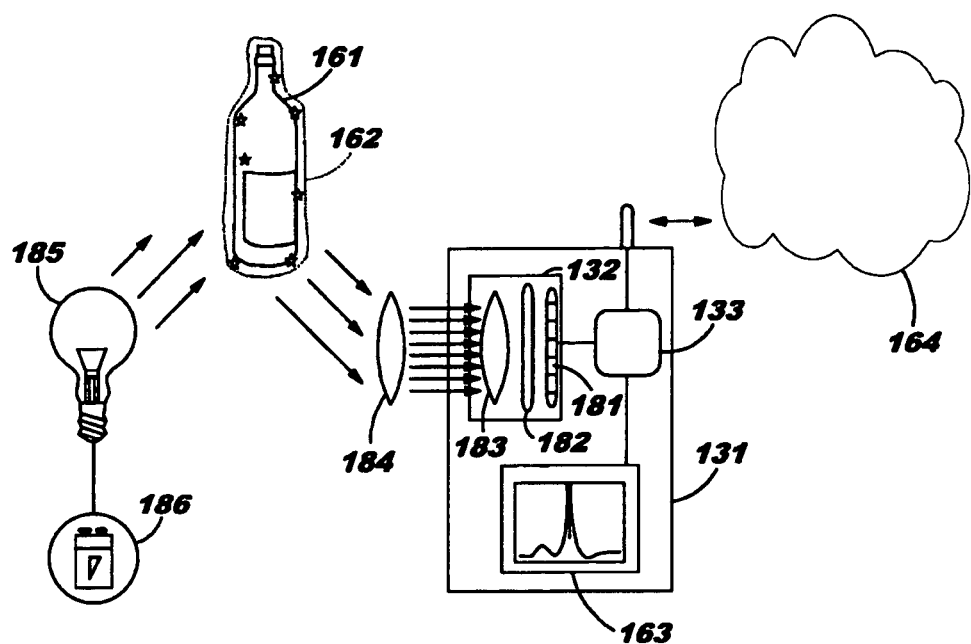
FIG. 13 shows schematically a smart phone serving a spectroscopic function according to the invention.

FIG. 13 shows schematically a smart phone 131 serving a spectroscopic function according to the invention. A package 161 is shrink-wrapped in shrink-wrap material 162 joined with taggants. A light source 185 powered by an energy source 186 illuminates the package 161 and illuminates the taggants. Light from the taggants reaches (in this embodiment) a first lens 184 and then through a collimator (omitted for clarity in FIG. 13), then through a second lens 183, then passes through a diffraction grating 182, and then forms an image on imaging array 181. The detected image 181 reaches processor 133 which carries out an analysis in a memory yielding spectroscopic image 163. The image itself, or information derived from the image, is communicated wirelessly through cloud 164 for various purposes as described in more detail below.

It should be appreciated that product 161 is exemplary as a bottle surrounded by shrink wrap 162. But it could be many other things such as a medicine in drug packaging or a bag as described above.

It will be further appreciated that the specific design of spectrometer 132 may be varied without departing in any way from the invention. Any of a multiplicity of optical paths will serve as needed to develop a spectrographic image at detector 181.

Figure 6:
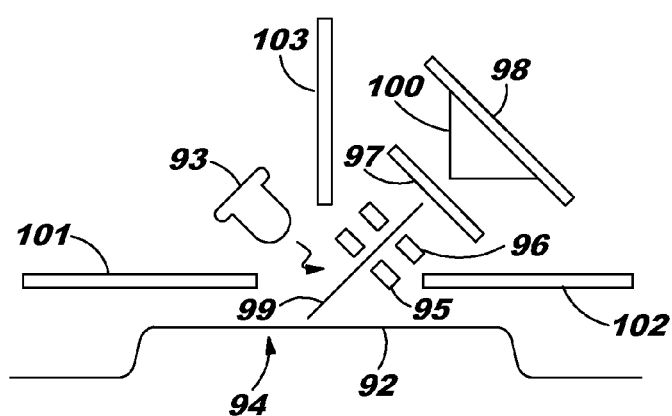
FIG. 6 shows in cross section an embodiment of the spectroscope according to the invention.

Turning now to FIG. 6, we see in cross section an embodiment 91 of the spectroscope according to the invention. An authentication material 92 is stimulated or illuminated at analysis region 94 by a light source 93, for example an LED (light-emitting diode). Light of interest (perhaps reflected light or light resulting from fluorescence) passes along path 99 through first slit or pinhole opening 95 and second slit or pinhole opening 96, serving to collimate the light of interest. Diffraction grating 100 spreads the collimated light to form a spectrographic image at imaging array 98. Baffles 101, 103, 102 serve to reduce stray ambient light reaching the path 99, and serve to reduce stray light from the source 93 reaching the path 99 other than after interacting with the authentication material 92.

Again the alert reader will appreciate that there are many ways to collimate light other than two slits or pinhole openings, and that there are many ways other than a diffraction grating to spread collimated light to form spectrographic images, all without departing from the invention.

Figure 7:
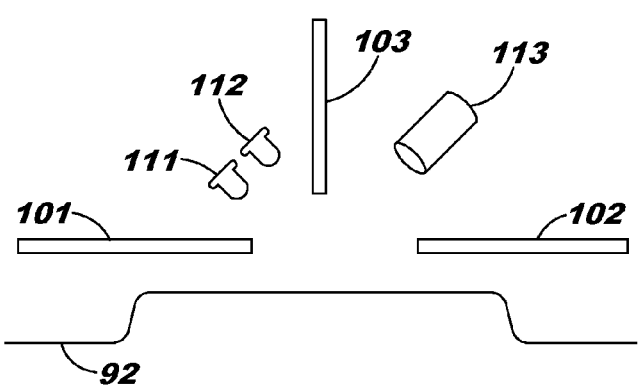
FIG. 7 shows in cross section another embodiment of the invention.

FIG. 7 shows in cross section another embodiment 114 of the invention. A sensor 113 may be colorblind and may be disposed to pick up light that has interacted with authentication material 92 after being illuminated or stimulated by a plurality of light sources 111, 112. The light sources are illuminated one after the other, each generating light of associated wavelength or wavelengths. The system keeps track of the intensity of light received at sensor 113 at the times when one or another of the light sources 111, 112 is turned on. In this way spectrographic activity may be detected. The number of light sources is here depicted as two but a larger number may be employed. As compared with the embodiment 91 of FIG. 6, the embodiment 114 of FIG. 7 has a less expensive sensor 113 but has a more expensive source of illumination or stimulation light. A number of factors relating to cost, physical size, and functional needs may affect a designer's choice of an approach more like that of FIG. 6 or an approach more like that of FIG. 7.

Figure 8:
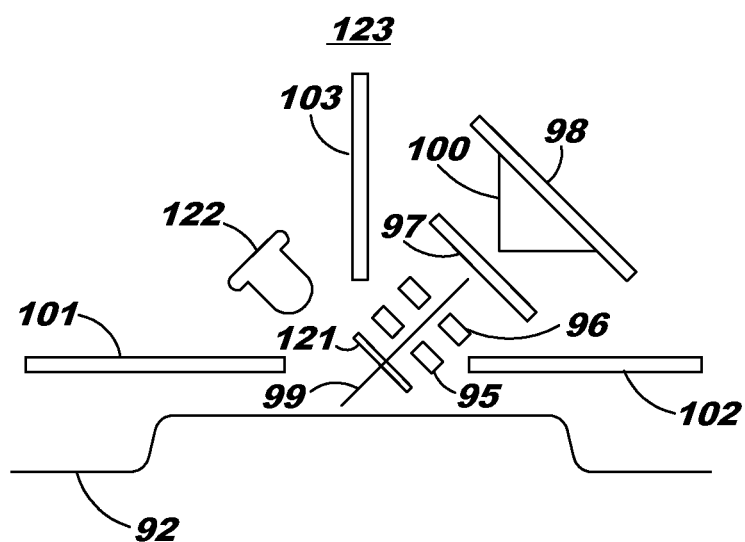
FIG. 8 shows in cross section yet another embodiment of the spectroscope according to the invention.

FIG. 8 shows in cross section yet another embodiment 123 of the spectroscope according to the invention. In this embodiment at least some of the spectrographic activity being probed is fluorescence. A light source 122 emits light of a first wavelength which stimulates the authentication material 92. One or more taggants fluoresce, emitting light of a second wavelength, longer than that of the first wavelength, some of which passes along light path 99. In this embodiment a filter 121 blocks some or most of the light of the first wavelength. Helpfully, this filter 121 improves the signal-to-noise ratio for some aspects of the sensed spectrographic image at sensing array 98.

Figure 9:
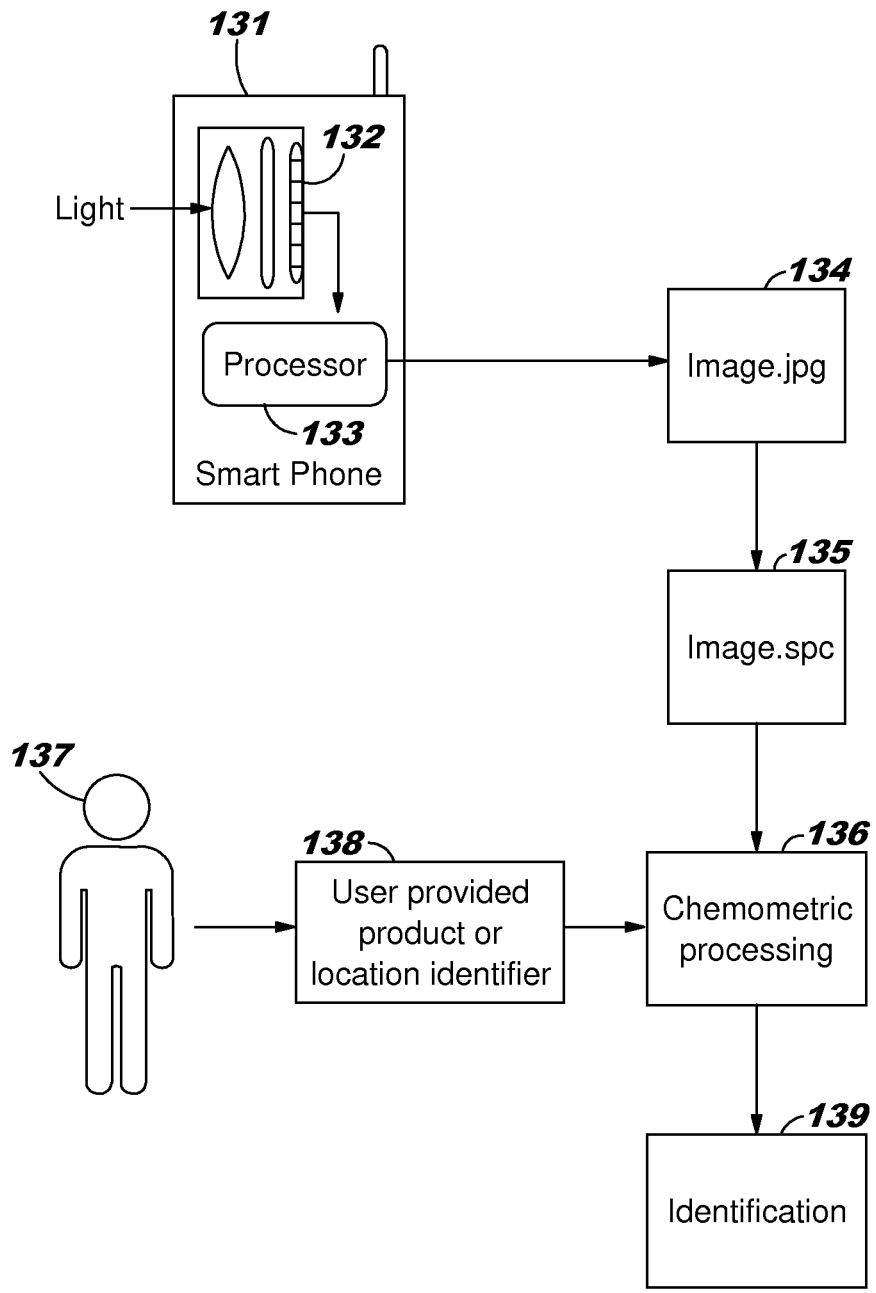
FIG. 9 shows a data processing flow according to one embodiment of the invention.
Figure 10:
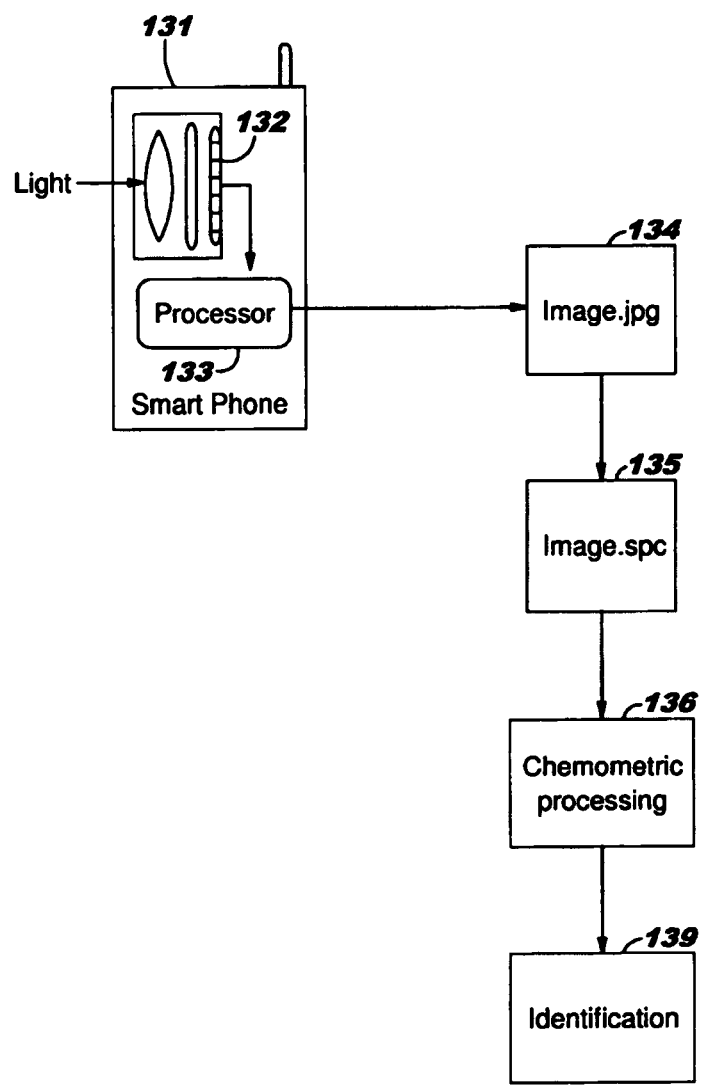
FIG. 10 shows a data processing flow according to another embodiment of the invention.

FIG. 9 shows a data processing flow according to one embodiment of the invention. A processor 133 in smart phone 131 captures a spectroscopic image 134 which may be a JPG file, about which more will be said below. The processor 133 generates an SPC file, about which more will be said below. A user 137 provides product or location information 138 which contributes to chemometic processing at 136 leading to identification 139 of a product or package. FIG. 10 shows a data processing flow according to another embodiment of the invention again arriving at an identification 139 of a product or package.

Figure 14:
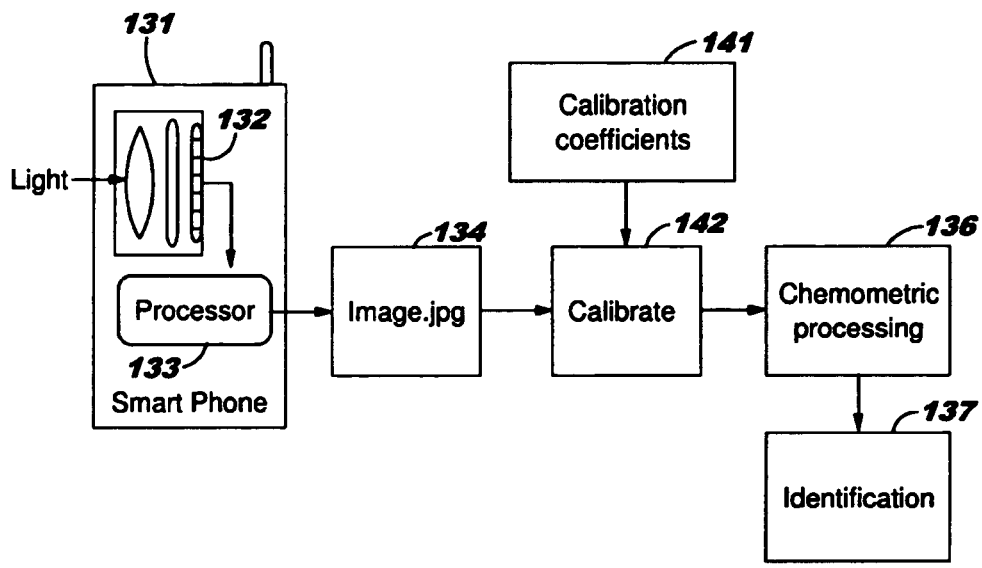
FIG. 14 shows a data processing flow according to yet another embodiment of the invention.
Figure 15:
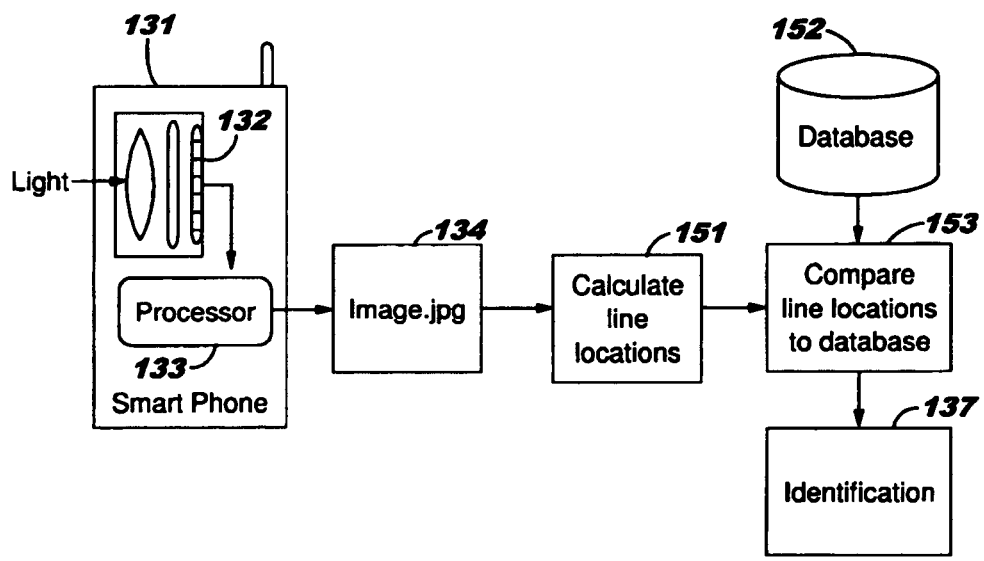
FIG. 15 shows a data processing flow according to still another embodiment of the invention.

FIG. 14 shows a data processing flow according to yet another embodiment of the invention. In this embodiment, calibration coefficients 141 are drawn upon to permit calibration 142 of analysis of the raw image 134. FIG. 15 shows a data processing flow according to still another embodiment of the invention. In this approach, the processor works out the location of particular spectrographic lines (which might be absorption lines for example). A database 152 is consulted and a comparison 153 is made of the detected lines with lines in the database 152, yielding an identification at 137.

The above discussion of the data processing flow of FIG. 14 assumes that the database 152 is located within the smart phone 131, and that the calculation 151 and comparison 153 take place within a processor within the cell phone 131. The alert reader will, however, have appreciated that considerations of security, privacy, or cost optimization may prompt offloading all or part of the calculation and comparison steps, as well as storage of the database 152, to a remote host located somewhere in a cloud 164 (FIG. 13), with communication between smart phone and said host secured by encryption such as public-key encryption. Many such approaches will serve as a variant of the invention but will not depart from the invention.

Figure 11:
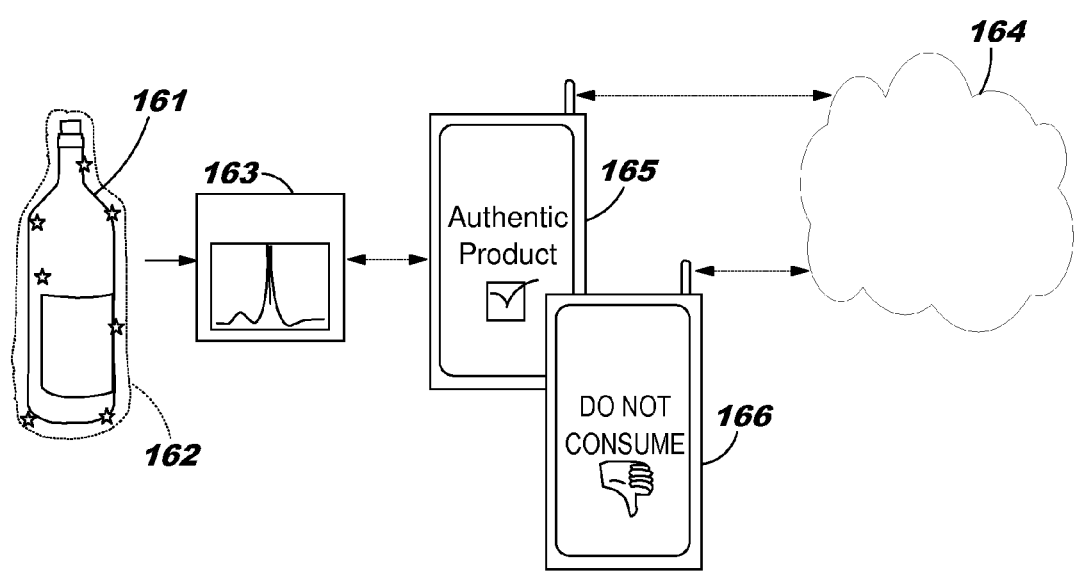
FIG. 11 shows a go/no-go sequence of events from the point of view of a user.

FIG. 11 shows a go/no-go sequence of events from the point of view of a user. The user employs the smart phone to test a product, and detected spectrographic activity permit a finding 165 of an authentic product or a finding 166 of a counterfeit or tampered-with product. The finding is communicated (by cloud 164) to a remote host, omitted for clarity in FIG. 11, at which for example a geographic map (again omitted for clarity in FIG. 11) may be developed showing geographic areas where counterfeit products have been found.

To this end the user apparatus comprises a spectrometer, the spectrometer disposed to sense respective magnitudes of spectroscopic activities. There is also a comparator means comparing sensed respective magnitudes of spectroscopic activities with a predetermined threshold, thereby determining which taggants, from among the plurality of taggants, are detected. There is also a computational means responsive to the detected taggants for assembling "one" bits corresponding to the bit positions associated therewith, yielding a binary number. There is also an annunciation means annunciating to a user an annunciated result indicated by the binary number.

Figure 12:
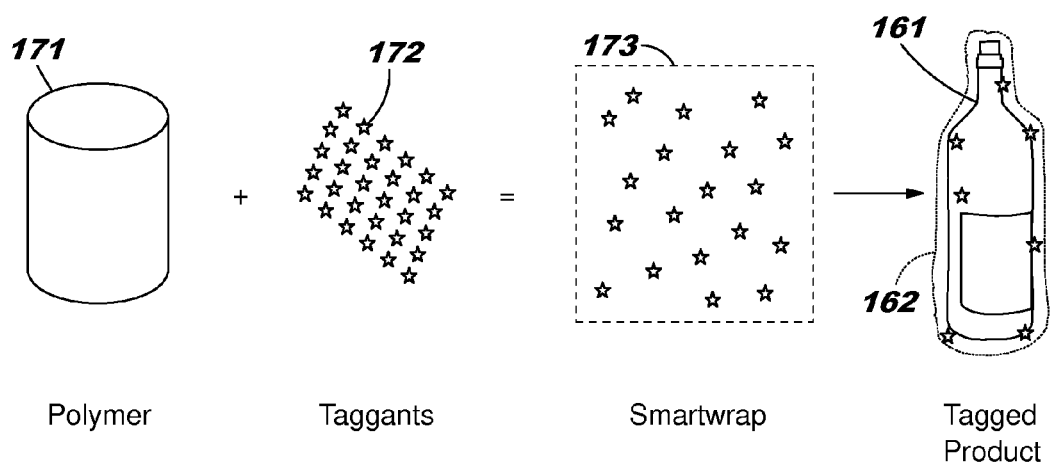
FIG. 12 shows materials and schematic steps leading to an authentication medium on a consumer product.

FIG. 12 shows materials and schematic steps leading to an authentication medium on a consumer product. A bulk polymer 171 is melted or dissolved and mixed with taggants 172 here shown schematically as stars. The mixture is extruded or calendared into a smart wrap 173 which has the taggants 172 disposed within. The wrap 162 may then for example be shrunk onto product 161. In this approach the taggants 172 are within the medium, but as mentioned above, the taggants might instead be applied or affixed to one surface of the sheet-formed polymer, for example by spraying or sputtering. This surface may then be an inner surface or an outer surface when the wrap is laminated or shrunk into place, or is itself used for packaging purposes.

What we end up with typically is a package, the package having an authentication material placed thereon, the authentication material having joined to it a plurality of taggants, each taggant having a respective spectroscopic activity.

The discussion above assumes for simplicity of narrative that the spectrographic activity for each taggant which might or might not be present is successfully tested for. In plain language it assumes for simplicity of narrative that each "1" or "0" sensed result is successful. It will be appreciated that experience and design factors may prompt a system designer to include some error tolerances in the system. For example a sensed result that deviates by one particular item of spectrographic activity (for example one particular absorption line) from an expected result might nonetheless be counted as a match. As another example the system may try moving the threshold 46 (FIG. 1) upwards or downwards in a particular case to accommodate particular conditions. Field data may indicate that for some production run of authentication media, some particular absorption line turns out not to be consistently visible, and real-time updates may be provided to smart phones instructing the smart phones to ignore that particular line when carrying out authentication with respect to that production run.

More can be said about applications of the invention, for example in a first embodiment relating to product verification. A supplier identifies a product. The product itself may have measurably distinct native spectral properties or it may be tagged with a taggant. The taggant has measurably distinct spectral properties. The taggant may be imbued in the wrapping of the product or it may be applied to the product or packaging. For example the taggant may be applied by vapor deposition, ink, a sticker, within the plastic of a container, shrink-wrap, or collar, or as a liquid dispersed in a liquid product.

A consumer selects the product for verification. The consumer may include an intermediate party or auditor and is not necessarily an end user or purchaser. The consumer detects at least one spectral property of the product or tagged material.

Detection may occur by several methods. In some embodiments a broad spectrum illumination source illuminates the product. Light returning from the product is collimated and formed into a spectral image.

In one embodiment a phone-based spectrometer generates a standard image file, in a format such as .jpeg. The .jpeg format file is converted to a spectroscopic file, in the emerging-standard .spc format, using conversion software. These .spc files can be analyzed using a variety of commercially-available chemometric (chemical mathematics) packages, including CAMO Unscrambler and Umetrics, resulting in a determination of whether the input matches an expected "gold standard" or not, i.e. is chemically equivalent to what it is expected to be. In some embodiments, images undergo conversion from a raster image file format, such as JPEG, JPEG2000, or emerging formats such as WebP, to AnIML, NIST's XML-based analytical instrument data standard. For analytical purposes, broadband can be converted to discrete wavelengths.

Detected spectral characteristics are then processed and analyzed. Processing and analysis may occur on the detector, on a remote processor, or on multiple remote processors. Different steps of the processing and analysis may be performed in different locations by various processors. The spectral data may be compared with a reference data set to determine whether the detected value matched an expected value. The presence or absence of a match is used to determine authenticity.

In many embodiments a consumer enters both the detected spectral data and at least one secondary data point. Secondary data may include information such as a product or location identifier. Examples of such identifiers may include, but are not limited to one or more of the following: a product name, serial number, lot number, barcode, universal product code (UPC), a uniform resource locator (url), a radio-frequency identification (RFID) signal, address, company name, brand, global positioning system (GPS) location, etc.

Second Embodiment

Smart Wrap

To form a smartwrap with taggants incorporated into the wrap polymer, polymer additives should be chosen to be either soluble or dispersible. Their melting point should be compatible with that of the polymer, and they should be able to withstand heating to 235° C., without charring, for at least several seconds as part of the wrap manufacturing process. In some embodiments, the additives should not be visible in the wrap, which is transparent and usually colorless. For additives such as silica, nano- or micro-versions may be preferred, so that white dots are not visible in the finished wrap. The best polymer additives are inexpensive and food-safe. The items on the FDA's GRAS (Generally Recognized as Safe) list would seem to be natural candidates, but in fact many have disqualifying characteristics. For example, sugars and starches burn during formulation and kaolin can leave visible marks in the finished product. Organic salts are good candidates for taggant compounds.

Typical polymer choices are polyethylene and polypropylene.

Alternate methods of incorporating the additives into the polymer, for spectroscopic detection, include spraying on the inside of the wrap, and vapor deposition on the outside of the label. These methods have the advantage of not requiring the chemicals to withstand the temperatures required to melt plastics. These methods may be particularly useful for taggants that are selected specifically because they are temperature sensitive.

In one embodiment, microencapsulated taggants are released by a temperature change, such as freezing, and react upon release in a way that may be detected by a spectrometer. The reaction may be with the air, such as by oxidation, or reaction with the polymer, or with other taggants. Preferably, the reaction is not easily reversible within the wrap material and the presence or absence of a reaction occurring may reliably indicate deviations from desired storage conditions since the wrap with taggants was applied. In one embodiment, a taggant chemical changes if exposed to a predetermined temperature, such as a temperature above a standard refrigerator temperature 5° C. (40° F.) such that the spectral properties of the taggant chemical are then measurably altered.

Experimental methods have shown positive results on a small scale by using flasks to melt the polymer and taggant together, in a nitrogen atmosphere to limit scorching. Using small beakers or flasks with stir bars on hot plates, the polymer was melted, the chemicals added, blending the polymer and chemicals by stirring, then the result poured onto aluminum foil, and rolled out to make thin films. On an industrial scale, the procedure would use larger volume containers, rollers, and other known techniques. If the chemicals added are not to be dissolved, they would preferably be evenly dispersed.

Examples of taggant chemicals include:
citric acid anhydrous
sodium benzoate powder
anthracene 98+%
caffeine
silica
potassium acetate
sodium citrate
sodium potassium tartrate A calibration equation is made by:
1. Using the main polymer as a matrix, add known amounts of the selected taggants.
2. Create the series of shrink wraps, remembering that shrinkage changes the spectra. One could create "before and after" scans for reference.
3. Scan the calibration wraps and save the spectra.
4. Correlate the "known" amounts of each ingredient to the correct spectra.
5. Use this calibration data to generate a chemometric equation, using good chemometric/statistical methodology.
6. Scan a series of "unknowns" prepared specifically for this project. Preferrably, these should not be the same lots used to generate the equation. Fewer samples are needed than the calibration set, but they should cover the range of values, especially for near infrared (NIR), which does not extrapolate well.

Third Embodiment

Direct Measurement

Since there are many variations among dosage forms, even when made by the same manufacturer at different production sites, simple spectrometric identification could be difficult. It might involve many hundreds of scans by an analyst and computer manipulations. If one assumes that the same type of equipment would be used by every investigator, then the database would be worth building. Since there is not a concerted effort, and most agencies and drug manufacturers are using different assay methods, there would not be much overlap among investigations.

Fourth Embodiment

Binary Code Smartwrap

This may be done by adding a series of up to, in an exemplary embodiment, seven chemicals, in small portions, to the shrink wrap material. The identities and proportions of the materials added are known to the manufacturer, but are not common knowledge. By adding above the detection level or not adding the chemicals, a unique combination may be created.

If the order of chemicals is predetermined, then they may be read in an order simulating a binary code. Assume we use six taggants: identifying them as "a" through "f." Then the order for them to be seen/identified by either a near-infrared or Raman spectrometer (or other chemical analyzer or detector) would be f, e, d, c, b, a (binary is often read from right to left). If a material is present, then a "1" is assigned to it; if absent, a "0" is assigned. For a material containing taggants a, c, and f and not containing b, d, or e, using place value, the code would be 100101.

Binary is simply a series of 2 to a given power. The first number on the right is 2 to the 0th power or "1" (any number to 0th power=1), the next to the left is 2 to the 1st power or simply 2. The next is 23 or 8, and so forth. The binary number derived from the chemical code is simply multiplied by the values of 1 or 0. For example, in the above coded material, $$[(f) \times 25] + [(e) \times 24] + [(d) \times 23] + [(c) \times 22] + [(b) \times 21] + [(a) \times 20] =$$

$$[(1) \times 25] + [(0) \times 24] + [(0) \times 23] + [(1) \times 22] + [(0) \times 21] + [(1) \times 20] =$$

$$[1 \times 32] + [0 \times 16] + [0 \times 8] + [1 \times 4] + [0 \times 2] + [1 \times 1] = 37$$

In this case, the sample is identified as lot 37 of product "X." As a secondary security measure, some of the chemicals may also be used as part of the identity code. In other words, a letter could be a number or a letter, as determined by a key only the company security department knows. As an example, the above product code can be altered, by changing the taggants, to $$[(1) \times 25]/[(e) \times 24]/[(d) \times 23]/[(1) \times 22]/[(b) \times 21]/[(1) \times 20] = 32 + e + d + 4 + 2 + 1 = 32ed421$$

Or $$32 + 16e + 8d + 4 + 2 + 1 = 3216e8d421$$

As long as the key to the code is predetermined and known to the inspector, any of these combinations may be used. The total number of letter/number combinations can be increased by simply changing the letter assigned to each taggant at a regular interval.

The manner in which the materials are used is as follows:
1. Decide on the code(s) which a manufacturer wishes to use. Assign an order to the ingredients (e.g. "A" through "F") and set the levels able to be determined (based on standard error of the chemometric equation: for example, can we read the value with an accuracy of +0.01% or +0.2%?).
2. Use a code for the levels, for instance, if the levels range from 0% to 5% and you can read accurately enough, the levels can be set at increments of 0.5. This would give values of 0 for 0, 1 for 0.5%, 2 for 1.0%, 3 for 1.5%, and so forth.
3. The read-out can be set to read, as an example, 1-3-2-5-7-2.
4. Individual components can also be used as letters, giving 1-3-b-5-g-2 for greater numbers of alphanumeric identifiers.
5. Further increase the number of identifiers by reversing the order of analysis. The above example would then be 2-g-5-b-3-1 and be distinct from the first value.

As far as analysis techniques, a mixed mode is possible:
1. NIR could be used for 3, 4, or 5 components and fluorescence for one or two others. This would add to specificity and could be used for product identity in addition to lot number.
2. UV, Visible, NIR, and fluorescence are good choices in the described embodiment for fast analysis. Other techniques could be used where, say, a loading dock or a mobile lab (van/truck) is the point of analysis.

An alternate workflow for creating smartwrap is as follows:
1. Analyze candidate ingredients for use in smartwrap recipe A.
2. Ensure that sufficient ingredients in recipe A have distinctive chemical attributes that can be distinguished using the selected instrumentation, e.g. spectroscopy.
3. From the ingredients in Step 2, create a series of carefully measured "known" ingredients.
4. Develop a calibration curve, so that combinations of the chemicals in recipe A can be determined, anywhere (including in the range of 100,000 to 1,000,000 combinations)
5. Calibrate the selected instrument to measure mixtures of the chosen chemicals
6. Take chemical signature of recipe A smartwrap
7. Assign coded information to said chemical signature, storing in database
8. Verify smartwrap and decode it by using the selected instrument and referring to the values in the database
9. Coordinate with other data using multisource fusion An example of an exemplary embodiment on a mobile device would be:
1. It contains a silica-based spectrometer (capable of collecting spectral data from wavelengths that range from visible light through 1000 nm)
2. It has an App for reading bar codes.
3. It has the ability to work in a network (base computer system) (store the code data in the cloud)

This means that a client could read a bar code, send it to a central location, and have it recognized by the software. The correct "binary" code (alphanumeric) is then sent back to the phone. The spectrum can be run on the spot and the code compared immediately, giving a yes-or-no answer. In other words, the device would serve as an all-in-one unit. For security and simplicity, the "code" is never disclosed to the person at the application end, avoiding bribery and blackmail. Other advantages over a separate spectrometer and variable amounts would be the ease of library creation: binary is much easier to detect, and much easier to compare across different brands and types of analytical instruments.

An additional application ("App") is the ability of the camera/phone/spectrometer to send the spectrum as a .jpeg file and allow the bar code and spectrum to be matched remotely, e.g. on the "home computer," or in the cloud, rather than on-board. This remote matching has certain advantages, including 1) making the units simpler to construct and modify and 2) keeping proprietary information secret, in the sense that buying/leasing the equipment would not give a competitor access to any of the software used for matching.

Track-and-trace methods increasingly include a step of marking a package in some way (e.g. RFID, bar code, 2D bar code), and verifying the code by accessing a database, thereby confirming that the coded package contains a legitimate mark (serialization, code, or number). The limitation of this packaging-based track-and-trace is, as noted, that it fails to protect against illicit activity that tampers with the product but reuses and reseals the package. The invention described here offers an additional layer of verification. As an analogy, when a credit card is verified, the merchant transmits the card number to a database, which returns a code. The merchant records the code; without it, the transaction is invalid. In the case of product verification, the track-and-trace code, which we will call Code 1, is conveyed to a database, which returns a code, Code 2, that is expected to match either the smartwrap code or, potentially, a code derived from an analysis of the product itself. The product analysis code might, for example, come from a spectroscopic analysis of the products inside the container, or from tiny RFID or RFID-like transmitting taggants on the product itself or in the product substance. The smartwrap code or product analysis code is collected in the field; in exemplary embodiments it is collected quickly and easily with a handheld instrument. As in the credit card case, the merchant (or other verification agent) must confirm that Code 2 matches the field-collected code. If it matches, the product is legitimate. If it does not, the product is assumed to be altered (counterfeited, tampered), and should not be purchased or used.

The field-collected code may also include mechanisms for recording damage to the product. For example, it may rely on a chemical that breaks down if the cold chain is violated. In that case, the field-collected code would fail to match the expected Code 2, because the product had gotten too warm or too cold and was no longer safe to use.

Exemplary Applications and Uses

Advances in analytical technology, along with the advent of portable communication devices, can restore customer reassurance by putting that technology to work along the product and food supply chain. Using the hardware, communications, and analytical capability of a device, such as a smartphone, the instant method creates a portable verifier. For the patient who wants to know if a drug is counterfeit, the parent who worries that a toddler has been poisoned by the capsule she just grabbed, or the consumer who is concerned about food tampering or pesticide residues, portable verification brings peace of mind. For public health officials, aggregated, locationally and temporally tagged information makes it easy to track consumer concerns and spreading problems.

Consumers are rewarded with coupons and encouraged with game mechanics, to make being a citizen inspector more fun. For example, a user can become the "drug czar" of a particular location. The verification system may include advertisements. Consumers can use described methods to check, for example, whether a product has been recalled, whether they are allergic to its ingredients, whether it is organic, or whether it fits into their diet given what they have already eaten that day. It can also aid as an early warning system for medication errors.

A use of the invention could be a two-stage test for drug use: first, the accelerometer and game features of the smartphone could be used to determine that the test subject's coordination was impaired, and then an analytical test could determine that an illegal drug was present.

Most spectroscopy applications use qualitative analysis, but it is also possible to employ multicomponent quantitative analysis. The multivariate algorithm used by the instrument, previously calibrated, then determines the precise levels of each of the ingredients and can have this information presented as a code, such as a bar code or alphanumeric string, which can represent the product, lot number, production location, product strength, date of production, expiry date, to name some data needed to specify a "proper" or authentic product. Up to a dozen ingredients may be simultaneously measured with a chemometric model in milliseconds.

As a further elaboration of the idea of multisource fusion, products and containers, for example bottles of pharmaceuticals or vitamins, may be considered as a source of information as to the actual contents since they arise at some point in time simultaneously; that is, they are brought together at a place and time that confer upon them geolocational information. For example, "Is this bottle, with this drug in it, supposed to be here at this time?" Is the supply chain functioning efficiently? Has product diversion occurred? Is this a gray-market good?

Knowing that a single tested drug is inauthentic gives a user feedback on whether it is a good idea to take the drug (no), but integrating multiple results, along with geographical information, historical crime data and trends, and a severity analysis, incorporating chemical information and perhaps consulting pharmaceutical science experts, creates a municipal health and safety action plan that can be implemented quickly and protect the public.

Described layered verification methods can be used for continuous inventory monitoring, also known as perpetual inventory monitoring, for example for a stock of controlled substances. In an exemplary embodiment, RFID chips would transmit signals; any change in the signals would set off an alarm indicating that the inventory had been altered in some way.

A user approaches a consumer product, collects spectroscopic data from the consumer product using a phone spectrometer, collect at least one additional sensor input using said phone spectrometer, and use an algorithm to produce a result. The sensor information may include, but is not limited to, visual information as captured by a camera, analytical information as captured by an infrared, near infrared (NIR), ultraviolet/visible or fluorescent source and detector, data acquired via a barcode reader, geolocational and time information, and gyroscopic, accelerometer, and proximity data.

A manufacturer formulates a marker for a plastic coating, said marker consisting of at least one non-essential additives that melts or disperses homogenously in the plastic, manufacture the plastic with the additives, wrap consumer products in the marked plastic, detect the presence or absence of the marked plastic in a wholesale or retail environment using a spectrometer, create a fraud alert in the case that the markings are not as expected.

A consumer approaches a consumer product, collects spectroscopic data from the wrapping of the product using a phone spectrometer, fuses the spectroscopic data with additional consumer data (date, location, identifier), and submits the fused information to determine if the consumer has received a prize.

A consumer or wine taster approaches a bottle of wine, uses a phone to scan its bar code, opens the wine and uses a phone spectrometer to take spectra of the wine itself, and compares it to a remote data store, receiving a response to determine whether the wine is genuine and in good condition.

A consumer approaches a food item, uses a phone spectrometer to take spectra of the food itself, and determines the fat content of the food; this information is then fused with stored data about the consumer's health needs and fat tolerance to generate a decision on whether the consumer should eat the item. A similar determination could be made for gluten or any allergen such as peanut.

A consumer approaches a food item suspected to be subject to a recall for safety reasons, uses a phone spectrometer to take spectra of the food itself; this information is then compared to a remote data store of recalled items, and the consumer receives a response to determine if the food is subject to the recall.

A user's pet eats an unknown medication. The user takes spectra with cellphone, transmits spectra to database in the cloud, receives back best match of drug name, incorporating drug name into search query automatically, creating a query to the Web of the form "What do I do if my dog ate Chemical-X?", receive veterinary advice back.

A user seeks information on the edibility of a wild mushroom. Take spectra with cellphone, transmit spectra to database in the cloud, receive back either recipes or an alert saying DO NOT EAT. Phone can also transmit time/location information to health authorities if needed.

A consumer approaches a drug item suspected to be subject to a recall for safety reasons, uses a phone spectrometer to take spectra of the drug item; this information is then compared to a remote data store of recalled items, and the consumer receives a response to determine if the drug is subject to the recall.

A consumer approaches a suspect food item, uses a phone spectrometer to take spectra of the food itself; this information is then compared to aggregated reports collected from social networking, and the consumer receives a response to determine if the food is safe to consume.

Is this drug counterfeit? A consumer approaches a suspect drug item, uses a phone spectrometer to take spectra of the drug item; this information is then compared to aggregated reports collected from social networking, and the consumer receives a response to determine if the drug is safe to consume. Transmit spectra to database in the cloud, receive back an ok with a manufacturer's coupon as compensation for the trouble, or receive back an alert saying DO NOT TAKE; phone transmits additional information (time, location, spectra of the counterfeit) for use by the manufacturer, public health authorities, and law enforcement to sketch the extent of the distribution of that particular counterfeit.

The smartwrap technique could be applied to products of any sort, whether in containers or not. It could also be applied to individual components, in-process materials, or finished products, particularly since many goods are started at one location, either at the manufacturer's location, another venue, or even an out-sourced plant/country. This would avoid adulteration and mismatched products.

Particular Approaches for Use of the Invention

A manufacturer or packager or distributor (for example) of a product selects a first identifier indicative of a first binary number comprising at least six bits. For each bit of the at least six bits of the binary number, we determine whether the bit is a "one" or a "zero". For each bit of the at least six bits that is a "one", we provide a respective taggant (from among a universe of possible taggants) having a respective spectroscopic activity, whereby said taggant is associated with a respective bit position within the at least six bits. The provided taggants are joined to a first authentication material which is placed upon a first package.

The first authentication material may be a shrink-wrap material, in which case we shrink the shrink-wrap material onto the package. In particular it may be a band, and the band may be placed at a sealing location of the package. For example the package may be a bottle with a screw-top cap at a neck thereof, in which case the sealing location is the neck of the bottle. Alternatively the first shrink-wrap material may surround some or all of the first package.

In another approach, the first authentication material is a sheet, and the first package contains a consumer product, and the joining step comprises laminating the sheet to a face of the package. For example the package may be is a flexible heat-sealed bag and the consumer product may be an edible or drinkable or consumable product within the bag.

In still another approach the package is a blister-pack, at least one blister containing a consumable product such as a pill.

The number of bits that is a "one" in the selected identifier may be at least two, or at least three, or at least four.

Once a selected identifier (and thus the corresponding selected taggants from among the universe of possible taggants) is selected, then the placing of the authentication material upon a package is repeated, perhaps a hundred times or a thousand times.

A testing step may then be carried out at the point where the authentication material is placed upon a package. In such testing, we carry out a spectroscopic analysis of the spectroscopic activities detected at the authentication material of one of the packages, thereby determining which taggants are detected. We assemble "one" bits corresponding to the bit positions associated with the detected taggants, yielding a second binary number. We can then compare the first binary number with the second binary number, and in the event of a failed comparison, we do not distribute the packages to the public. In the event of a successful comparison, we can distribute the packages to the public.

Later a similar testing step may be carried out by a member of the public. If the identifier developed from the testing satisfies a first predefined condition, the user avoids making use of any contents of the first package. If the identifier satisfies a second predefined condition, the user may remove at least some of the authentication material (for example a neck band on a bottle), and thereafter, the user may make use of contents of the package. The annunciated result may for example be communicated to the user visually or by means of synthesized speech.

In a typical embodiment, the respective spectroscopic activities of the taggants are not visible to the human eye, and the spectroscopic analysis is carried out by means of near-infrared spectroscopy. The number of taggants may be at least three or at least four, for example.

A remote host, distant from the user's smart phone or other handheld device, may carry out some or most of the analysis.

In one approach such a host receives from a user the results of a spectroscopic analysis of the spectroscopic activities detected at the authentication material of the package, determines from the received results which taggants, from among the plurality of taggants, are detected, assembling "one" bits corresponding to the bit positions associated with the detected taggants, yielding a binary number, the binary number indicative of an identifier, and arriving at a conclusion, based upon the identifier, regarding the authenticity of the package; and reports the conclusion to the user. The host may receive other information captured from the package, and the arriving at a conclusion step bases the conclusion not only upon the identifier but also upon the other information received from the user, for example by scanning a bar code on the package.

In a second approach a host receives from a user the results of a spectroscopic analysis of the spectroscopic activities detected at the authentication material of the package, the analysis comprising determining from the activities which taggants, from among the plurality of taggants, are detected, the analysis further comprising assembling "one" bits corresponding to the bit positions associated with the detected taggants, yielding a binary number, the binary number indicative of an identifier, the received results being indicative of the binary number. The host then arrives at a conclusion, based upon the received results indicative of the binary number, regarding the authenticity of the package, and reports the conclusion to the user. Again the host may receive other information captured from the package, and the arriving at a conclusion step bases the conclusion not only upon the identifier but also upon the other information received from the user, for example by scanning a bar code on the package.

The alert reader, prompted by the above discussion, will have no difficulty devising myriad obvious improvements and variations upon the invention, all of which are intended to be encompassed within the claims that follow.

The invention claimed is:

1. A method comprising:
   selecting an identifier indicative of a binary number comprising at least six bits;
   for each bit of the at least six bits of the binary number, determining whether the bit is a "one" or a "zero";
   for each bit of the at least six bits that is a "one", providing a respective taggant having a respective spectroscopic activity, whereby said taggant is associated with a respective bit position within the at least six bits;
   for the provided taggants, joining them to an authentication material; and
   placing the authentication material upon a package;
   wherein the authentication material is a sheet, and the package contains a consumer product, and the joining step comprises laminating the sheet to a face of the package;
   wherein the package is a flexible heat-sealed bag and the consumer product is an edible or drinkable or consumable product within the bag; and
   wherein at least one taggant changes if exposed to a predetermined temperature such that the spectral properties of the taggant chemical are measurably altered.

2. The method of claim 1 wherein the predetermined temperature is a temperature at or below the freezing point of water.

3. The method of claim 1 wherein the predetermined temperature is a temperature above the temperature of a standard refrigerator.

4. A method for use with a package having a sealing location, the package further having a authentication material upon the sealing location, the method carried out with respect to a plurality of taggants each having a respective spectroscopic activity, each taggant associated with a respective bit position, the method comprising the steps of:

carrying out a spectroscopic analysis of the spectroscopic activities detected at the authentication material of the package, thereby determining which taggants, from among the plurality of taggants, are detected;

assembling "one" bits corresponding to the bit positions associated with the detected taggants, yielding a binary number, the binary number indicative of an identifier;

in the event of the indentifier satisfying a predefined condition, making use of contents of the package; and further comprising the step, performed before the step of making use of the contents of the package, of removing at least some of the authentication material.

5. Apparatus comprising a package;

the package having an authentication material placed thereon;

the authentication material having joined to it a plurality of taggants, each taggant having a respective spectroscopic activity;

said taggant being an ingestible and covert commodity chemical;

wherein the authentication material is a sheet, and the package contains a consumer product, and the joining step comprises laminating the sheet to a face of the package; and wherein the package is a flexible heat-sealed bag and the consumer product is an edible or drinkable or consumable product within the bag wherein at least one taggant changes if exposed to a predetermined temperature such that the spectral properties of the taggant chemical are measurably altered.

6. The apparatus of claim 5 wherein the predetermined temperature is a temperature at or below the freezing point of water.

7. The apparatus of claim 5 wherein the predetermined temperature is a temperature above the temperature of a standard refrigerator.

8. A method for use with a package having a sealing location, the package further having an authentication material upon the sealing location, the method carried out with respect to a plurality of taggants each having a respective spectroscopic activity, each taggant associated with a respective bit position, the method comprising the steps of:

carrying out a spectroscopic analysis of the spectroscopic activities detected at the authentication material of the package, thereby determining which taggants, from among the plurality of taggants, are detected; and assembling "one" bits corresponding to the bit positions associated with the detected taggants, yielding a binary number, the binary number indicative of an identifier;

wherein at least one taggant changes if exposed to a predetermined temperature such that the spectral properties of the taggant chemical are measurably altered.

9. The method of claim 8 wherein the predetermined temperature is a temperature at or below the freezing point of water.

10. The method of claim 8 wherein the predetermined temperature is a temperature above the temperature of a standard refrigerator.

11. A method for use with a package having a sealing location, the package further having a authentication material upon the sealing location, the method carried out with respect to a plurality of taggants each having a respective spectroscopic activity, and each taggant associated with a respective bit position, the method comprising the steps of:

receiving from a user the results of a spectroscopic analysis of the spectroscopic activities detected at the authentication material of the package, determining from the received results which taggants, from among the plurality of taggants, are detected;

assembling "one" bits corresponding to the bit positions associated with the detected taggants, yielding a binary number, the binary number indicative of an identifier;

arriving at a conclusion, based upon the identifier, regarding the authenticity of the package; and reporting the conclusion to the user;

wherein at least one taggant changes if exposed to a predetermined temperature such that the spectral properties of the taggant chemical are measurably altered.

12. The method of claim 11 wherein the predetermined temperature is a temperature at or below the freezing point of water.

13. The method of claim 11 wherein the predetermined temperature is a temperature above the temperature of a standard refrigerator.

14. A method for use with a package having a sealing location, the package further having a authentication material upon the sealing location, the method carried out with respect to a plurality of taggants each having a respective spectroscopic activity, and each taggant associated with a respective bit position, the method comprising the steps of:

receiving from a user the results of a spectroscopic analysis of the spectroscopic activities detected at the authentication material of the package, the analysis comprising determining from the activities which taggants, from among the plurality of taggants, are detected, the analysis further comprising assembling "one" bits corresponding to the bit positions associated with the detected taggants, yielding a binary number, the binary number indicative of an identifier, the received results being indicative of the binary number;

arriving at a conclusion, based upon the received results indicative of the binary number, regarding the authenticity of the package; and reporting the conclusion to the user;

wherein at least one taggant changes if exposed to a predetermined temperature such that the spectral properties of the taggant chemical are measurably altered.

15. The method of claim 14 wherein the predetermined temperature is a temperature at or below the freezing point of water.

16. The method of claim 14 wherein the predetermined temperature is a temperature above the temperature of a standard refrigerator.

* * * * *

UNITED STATES PATENT AND TRADEMARK OFFICE
CERTIFICATE OF CORRECTION

| | | |
|---|---|---|
| PATENT NO. | : 8,517,274 B2 | Page 1 of 1 |
| APPLICATION NO. | : 13/522707 | |
| DATED | : August 27, 2013 | |
| INVENTOR(S) | : Emil Walter Ciurczak et al. | |

It is certified that error appears in the above-identified patent and that said Letters Patent is hereby corrected as shown below:

The title page, item [74] Attorney, Agent, or Firm should read as follows; the name of the Firm should be "Oppedahl Patent Law Firm LLC" instead of --Oppendahl--

Signed and Sealed this
Thirty-first Day of December, 2013

Margaret A. Focarino
*Commissioner for Patents of the United States Patent and Trademark Office*